US009044315B2

(12) United States Patent
Lopez et al.

(10) Patent No.: US 9,044,315 B2
(45) Date of Patent: Jun. 2, 2015

(54) SOFT TISSUE FIXATION DEVICE

(71) Applicants: Mandi J. Lopez, Saint Gabriel, LA (US); W. Todd Monroe, Baton Rouge, LA (US)

(72) Inventors: Mandi J. Lopez, Saint Gabriel, LA (US); W. Todd Monroe, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 14/094,906

(22) Filed: Dec. 3, 2013

(65) Prior Publication Data

US 2014/0236195 A1    Aug. 21, 2014

Related U.S. Application Data

(63) Continuation of application No. 11/461,214, filed on Jul. 31, 2006, now Pat. No. 8,603,115.

(51) Int. Cl.
*A61B 17/68*    (2006.01)
*A61F 2/08*    (2006.01)

(52) U.S. Cl.
CPC ....... *A61F 2/0811* (2013.01); *A61F 2002/0829* (2013.01); *A61F 2002/0864* (2013.01); *A61F 2002/0882* (2013.01)

(58) Field of Classification Search
CPC ........... A61F 2/0811; A61F 2002/0829; A61F 2002/0864; A61F 2002/0882
USPC ............. 606/280, 71, 283, 286, 297, 300, 75, 606/322, 86 R, 151, 219–221; 623/13.12, 623/13.14; 132/60, 61, 251, 273, 276, 278, 132/279, 280, 281
See application file for complete search history.

(56) References Cited

U.S. PATENT DOCUMENTS

| 2,502,034 A | 3/1950 | Gordon ........................... 24/108 |
| 4,291,698 A | 9/1981 | Fuchs et al. ................... 128/335 |
| 4,988,351 A | 1/1991 | Paulos et al. .................. 606/232 |

(Continued)

FOREIGN PATENT DOCUMENTS

WO    WO / 97 / 49341    12/1997

OTHER PUBLICATIONS

US 6,238,418, 05/2001, Schwartz (withdrawn).

*Primary Examiner* — Pedro Philogene
*Assistant Examiner* — David Comstock
(74) *Attorney, Agent, or Firm* — John H. Runnels; Bonnie J. Davis

(57) ABSTRACT

A soft tissue fixation device for use in ACL or CrCL reconstruction has a base member provided with a passageway extending perpendicularly from its top surface through its bottom surface. The passageway is sized to allow soft tissue to be inserted through the passageway. The fixation device also includes an affixing member attachable to the base member. The base member has a notched section in the top surface extending from the passageway to a first perimeter section of the base member sized to accommodate at least a portion of the graft. Either surgical grade tissue glue or at least one perpendicularly extending spike is used to secure the base member to the bone. The base member is also provided with a sleeve whose interior wall surfaces form a part of the passageway and is sized to be inserted into the bone opening. The affixing member is provided with a series of teeth members extending downward from its lower surface. The teeth members are positioned so that when the affixing member is attached to the base member the teeth members will extend across and into the notched section of the top surface of the base member. The opposite ends of the affixing member is shaped to fit into aligned notches positioned along perimeter sections of the base member bottom surface for attaching the clip member to the base member.

8 Claims, 14 Drawing Sheets

(56) References Cited

U.S. PATENT DOCUMENTS

| | | | |
|---|---|---|---|
| 5,078,731 A | 1/1992 | Hayhurst | 606/232 |
| 5,224,946 A | 7/1993 | Hayhurst et al. | 606/232 |
| 5,258,015 A | 11/1993 | Li et al. | 606/232 |
| 5,562,689 A | 10/1996 | Green et al. | 606/151 |
| 5,951,590 A | 9/1999 | Goldfarb | 606/232 |
| 6,066,160 A | 5/2000 | Colvin et al. | 606/232 |
| 6,132,442 A | 10/2000 | Ferragamo et al. | 606/151 |
| 6,235,057 B1 | 5/2001 | Roger et al. | 623/13.12 |
| 6,235,058 B1 | 5/2001 | Huene | 623/13.14 |
| 6,306,159 B1 | 10/2001 | Schwartz et al. | 606/232 |
| 2005/0096699 A1 | 5/2005 | Wixey et al. | 606/232 |
| 2006/0184200 A1 | 8/2006 | Jervis | 606/232 |

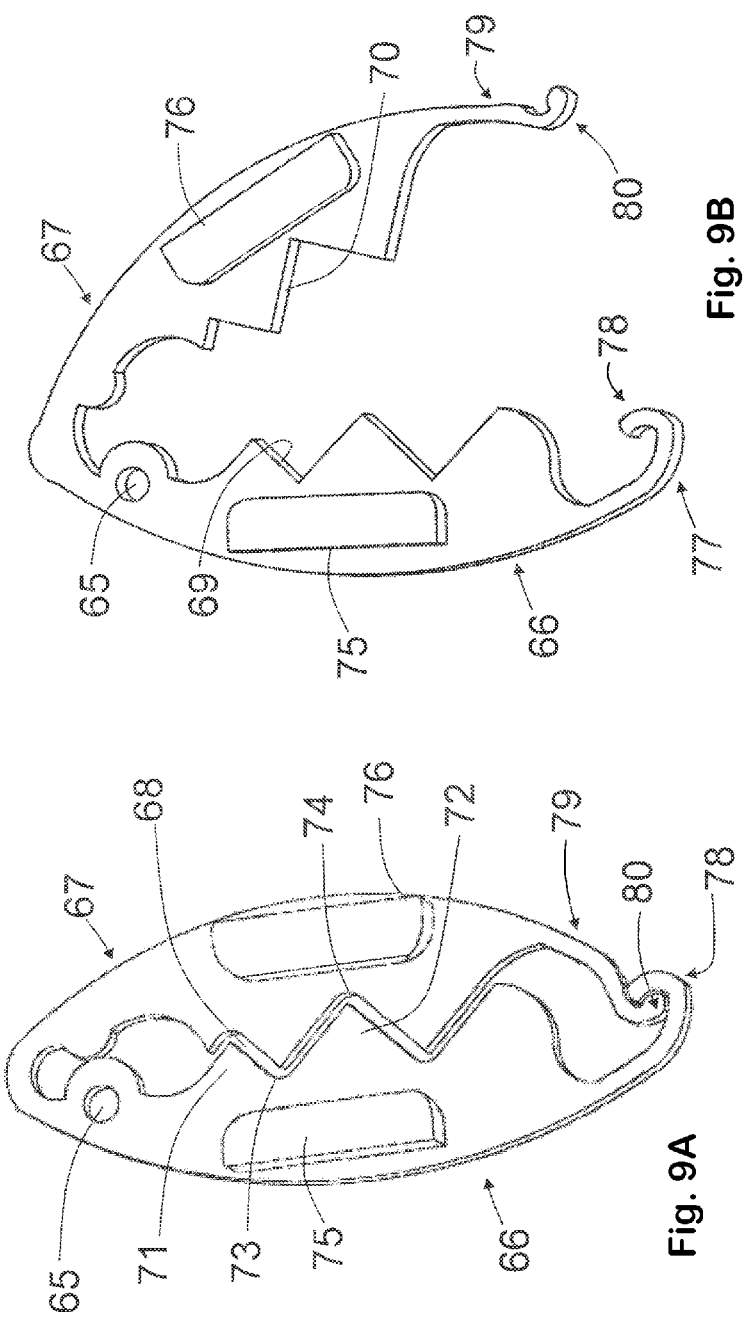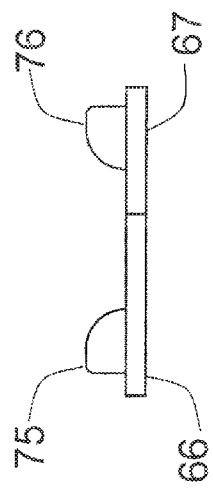

SOFT TISSUE FIXATION DEVICE

This is a continuation of patent application Ser. No. 11/461,214, filing date Jul. 31, 2006, now U.S. Pat. No. 8,603,115, the entire disclosure of which is hereby incorporated by reference.

BACKGROUND OF THE INVENTION

1. Field of the Invention

This invention relates in general to apparatus and methods to assist in the fixation of soft tissue to bone, and more particularly to human anterior cruciate ligament (ACL) and canine cranial cruciate ligament (CrCL) reconstruction grafts.

2. Prior Art

Rupture of the cranial cruciate ligament (CrCL) and subsequent osteoarthritis is a leading cause of canine hind limb lameness. Numerous techniques have been described to stabilize the canine knee or stifle following CrCL rupture to inhibit or prevent osteoarthritis. One such technique is intra-articular CrCL graft reconstruction for stabilization of CrCL deficient stifles. Various devices for initial surgical graft fixation have been utilized. These include the EndoButton CL, the Bone Mulch Screw, the RigidFix, Interference Screws, the BioScrew, the RCI screw, the SmartScrew ACL, a Synthes 6.5 cancellous screw with a spiked plastic washer or a soft tissue fixation plate, as well as various type staples, including stone and barbed staples.

In CrCL reconstruction it is necessary to obtain a desired graft tension and then to secure the tensioned graft at the desired position on the bone. There remains in the current surgical procedure problems with obtaining the necessary graft fixation strength quickly to prevent loss of the desired graft tension. A second problem relates to the damage of the graft as it is being tensioned over the rough or sharp surfaces of the bone or fixation device used. In addition the fixation device must have the ability to maintain the graft tension during the normal activity of the person or animal during the recovery period.

In the surgical application of these devices it is necessary that the graft to be affixed to the bone have the desired tension. The current devices are more difficult to employ during the surgical procedures than is desired. Therefore, there remains a need for a soft tissue fixation device that can be used with known arthroscopic or open surgical techniques, does not require unique application equipment, can be used with various CrCL reconstruction materials, and can affix the graft to the bone quickly and easily while still permitting the desired graft tensioning.

Still further there remains a need to provide a device that is simple in construction and would allow the CrCL reconstruction graft to be tensioned and secured to the bone in a single step.

OBJECTS AND SUMMARY OF THE INVENTION

Therefore, one object of this invention is to provide a soft tissue fixation device that can be used with known arthroscopic or open surgical techniques.

Another object of this invention is to provide a soft tissue fixation device that does not require unique application equipment Still another object of this invention is to provide a soft tissue fixation device that can be used with various ACL or CrCL reconstruction materials, such as from material that will over time become absorbed.

Another object of this invention is to provide a soft tissue fixation device that is resistant to axial and rotational movement during the tensioning and securing of the graft to the fixation device.

A further object of this invention is to provide a soft tissue fixation device that permits easier and quicker attachment of the graft to the bone while permitting the desired graft tensioning.

Another object of this invention is to provide a soft tissue fixation device that when attached to the bone maintains a low profile to reduce impingement on surrounding structure, as well as reduce the visibility of its presence under the skin.

Another further object is to construct a soft tissue fixation device that is simple in construction, and can be manufactured from absorbable materials by injection molding.

A still further object of this invention is to provide improved CrCL reconstruction procedures that permit the reconstruction graft to be tensioned and secured to the femur in one step without screws or staples.

Other objects and advantages of this invention shall become apparent from the ensuing descriptions of the invention.

Accordingly, this invention in one embodiment comprises a soft tissue fixation device for use in ACL or CrCL reconstruction comprising a base member having a top and bottom surface. The base member is provided with a passageway extending from the top surface through the bottom surface and sized to allow the soft tissue to be inserted into the passageway and extend out the opposite passageway end. The bottom surface of the base member is shaped to be attachable to the bone. In a preferred embodiment the top surface is shaped to present no sharp edges that a graft will contact during the surgical procedure. The fixation device also comprises an affixing member pivotally attached or otherwise attachable to the base member. The affixing member is constructed having a graft fixation section shaped to secure a tensioned graft between the base member and the affixing member.

In a preferred embodiment, the base member has a notched section in the top surface extending from the passageway to a first perimeter section of the base member. The notched section is sized to accommodate at least a portion of the graft in order for the fixation device to present a lower profile when used. In one preferred embodiment surgical grade tissue glue is spread on the bottom surface of the base member to secure the base member to the bone when the glue has dried. In another preferred embodiment the base member is disc-shaped with its substantially flat bottom surface having at least one perpendicularly extending spike shaped to permit it to be driven into the bone to which the graft will be affixed. The spikes are shaped to hold the base member rotationally and axially in position during and after the tensioning of the graft. In another preferred embodiment a sleeve whose interior wall surfaces form a part of the passageway extends perpendicularly from the base member bottom surface. The sleeve is sized to permit it to be inserted into the opening drilled into the bone to provide, along with the spikes, additional translational stability to the base member when the graft is being tensioned, as well as to prevent damage to the graft by the sharp edges of the bone tunnel.

In another preferred embodiment the affixing member is a clip having a generally arched shaped and provided with a series of teeth members extending downward from the lower surface of the clip member. The teeth members are positioned so that when the clip member is attached to the base member the teeth members will extend across and into the notched section of the top surface of the base member. In a more preferred embodiment the teeth members will extend beyond the notched section to better secure any portion of the graft that may lap out from the notched section. In this pre preferred embodiment the opposite ends of the clip member are shaped to fit into aligned notches positioned along perimeter sections of the bottom surface of the base member for attaching the clip member to the base member. This is accomplished by placing one of the clip member ends into its base member notch. Then through the use of a single, fluid type motion the affixing member is levered downward to force the opposite end into its base member notch thus securing the affixing member to the base member. In this embodiment it is preferred that the clip member be constructed from flexible material, such as an acetal copolymer or other material having similar flexibility characteristics.

In an alternate embodiment an improved surgical procedure for cranial cruciate ligament reconstruction is provided. In this embodiment the femur is prepared for receipt of the soft tissue fixation device in a conventional manner. This includes drilling a bone tunnel from the intra-articular origin of the CrCL to the center of the lateral aspect of the femoral condyle. The base member is aligned with the bone tunnel so that its sleeve is over the pilot hole. The base member is then tapped into place with an osteotomy mallet. If the base member is not provided with a sleeve, then the base member passageway is positioned over the pilot hole and secured in place with a sleeve, then the base member passageway is positioned over the pilot hole and secured in place with the use of surgical grade tissue glue. The graft is passed through the femoral tunnel and the sleeve. That portion of the graft extending from the sleeve is positioned across the top surface notch of the base member and pulled to achieve the desired tension. The pivoting end of the clip member is placed in one of the bottom surface notches. The clip member is then in one motion pivoted downward until the attaching end of the clip member is secured in the opposite bottom surface notch. This action causes the teeth of the clip member to grab the graft and secure the graft between the base member and the clip member sufficiently to maintain the desired tension.

BRIEF DESCRIPTION OF THE DRAWINGS

The accompanying drawings illustrate a preferred embodiment of this invention. However, it is to be understood that these embodiments are not intended to be exhaustive, nor limiting of the invention. They are but examples of some of the forms in which the invention may be practiced.

FIG. 9A is a top three-quarter perspective view of the affixing member of FIG. 9 illustrated in a closed position.

FIG. 9B is a top three-quarter perspective view of the affixing member of FIG. 9 illustrated in an open position.

FIG. 9C is a side view of the affixing member of FIG. 9B.

PREFERRED EMBODIMENTS OF THE INVENTION

Without any intent to limit the scope of this invention, reference is made to the figures in describing the preferred embodiments of the invention. Although the preferred embodiments of the invention will be described utilizing the invention in CrCL reconstruction, this in no way is meant to limit the invention to such use, as it will be appreciated it has use in ACL reconstruction and other human and animal applications.

Figure 1:
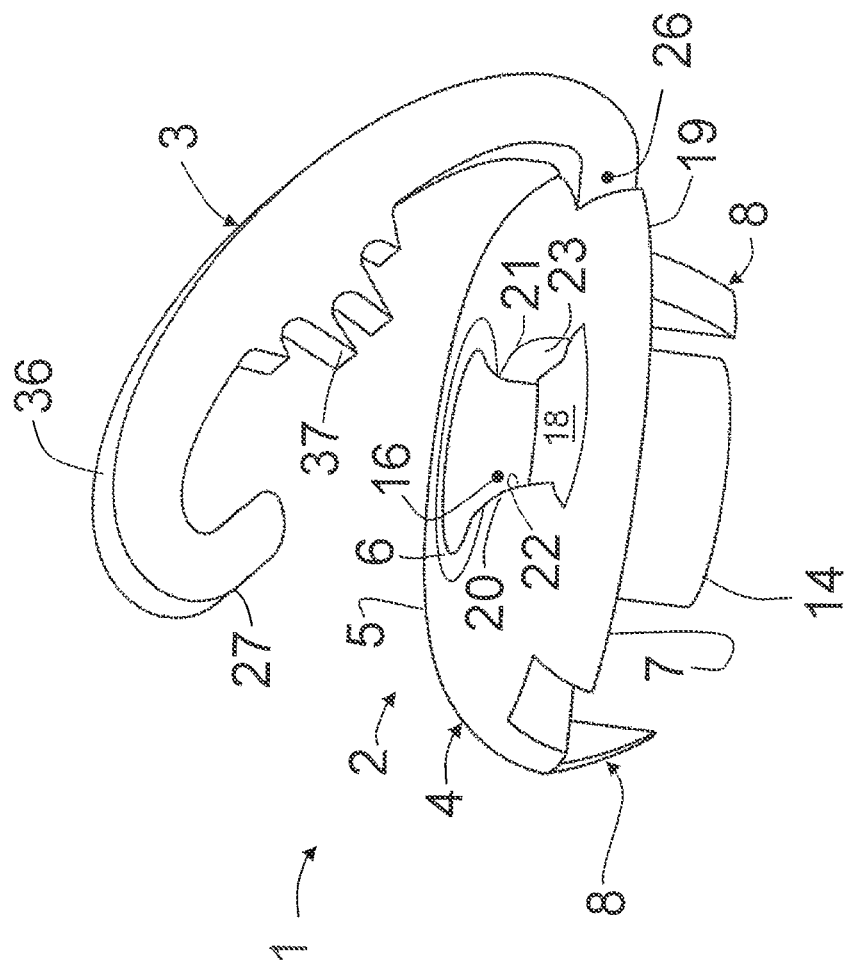
FIG. 1 is three-quarter top perspective view of a preferred embodiment of the soft tissue fixation device of this invention illustrated having the pivoting end of the clip member in position to be pivoted by the surgeon into an attached or locked position.

The device of this invention is particularly useful in ACL or CrCL reconstruction to fix a soft tissue graft to the bone of a human or dog suffering from an ACL or CrCL tear. Referring now to FIG. 1, a preferred embodiment of the soft tissue fixation device 1 includes a base member 2 and a graft affixing member 3. The primary function of base member 2 is to provide a stable platform to allow the soft tissue graft to be tensioned during the procedure to attach the graft to the bone. More particularly, base member 2 should be constructed to minimize the axial and rotational movement of the base member during the graft tensioning step. Base member 2 should further be constructed to minimize potential tearing of the graft during the tensioning step. On the other hand the primary function of affixing member 3 is to affix and maintain the soft tissue graft in the desired tensioned position on the base member 2.

That portion of base member 2 that will extend above the bone surface when attached to the bone is preferably is constructed to have a low profile. In a preferred embodiment base member 2 will be constructed having top surface 4 with a curved perimeter top surface section 5 surrounding a flat top surface center section 6 and a substantially flat bottom surface 7. The height of base member 2 must be such to permit the attachment of affixing member 3. Base member 2 may be secured in the desired position to the femur bone by the use of known surgical grade tissue glue. In another embodiment extending downward from bottom surface 7 is at least one securing member, such as spike R It is preferred that there be at least three spikes 8 equally spaced about the perimeter edge of bottom surface 7 to provide greater stability against rotation and lift forces on base member 2 during the tensioning of the graft. It is further preferred that spikes 8 be shaped to be easily driven into the bone, hold base member 2 in place during the tensioning of the graft, as well as minimize rotational and axial movement of base member 2 during the tensioning and securing of the graft to the fixation device 1. One preferred shape of spikes 8 is a tubular or solid shaped spike having a pyramidal shaped bottom section. Other shapes of spikes 8 include a tubular shaped spike with triangular cross-sectional shape bottom section. Spikes having a star-shaped tubular section can also be employed. If desired known surgical grade tissue glue can also be used in conjunction with a spiked base member 2.

The structural design of spikes 8 are preferably selected to provide ease of attachment to the bone while providing the desired stability to the base member 2 during the graft tensioning process. If desired there could be multiple rows of spikes 8. The shape of spike 8 must permit their insertion into the femur bone and to resist shearing caused by rotational forces on base member 3. In addition the shape of spike 8 should be resistant to upward forces that might cause base member 2 to become detached from the bone during the graft tensioning process. In one preferred embodiment these objectives are achieved utilizing spikes 8 having a substantially rectangular base 9 attached to bottom surface 7 with side 10 of base 9 tracking a portion of the perimeter of the bottom surface 7. The opposite side 11 of the base is provided with an arc-shaped portion 12 that with side 10 culminates to form a sharp edge 13. Other known shapes can be utilized that will provide the desired objectives.

Figure 2:
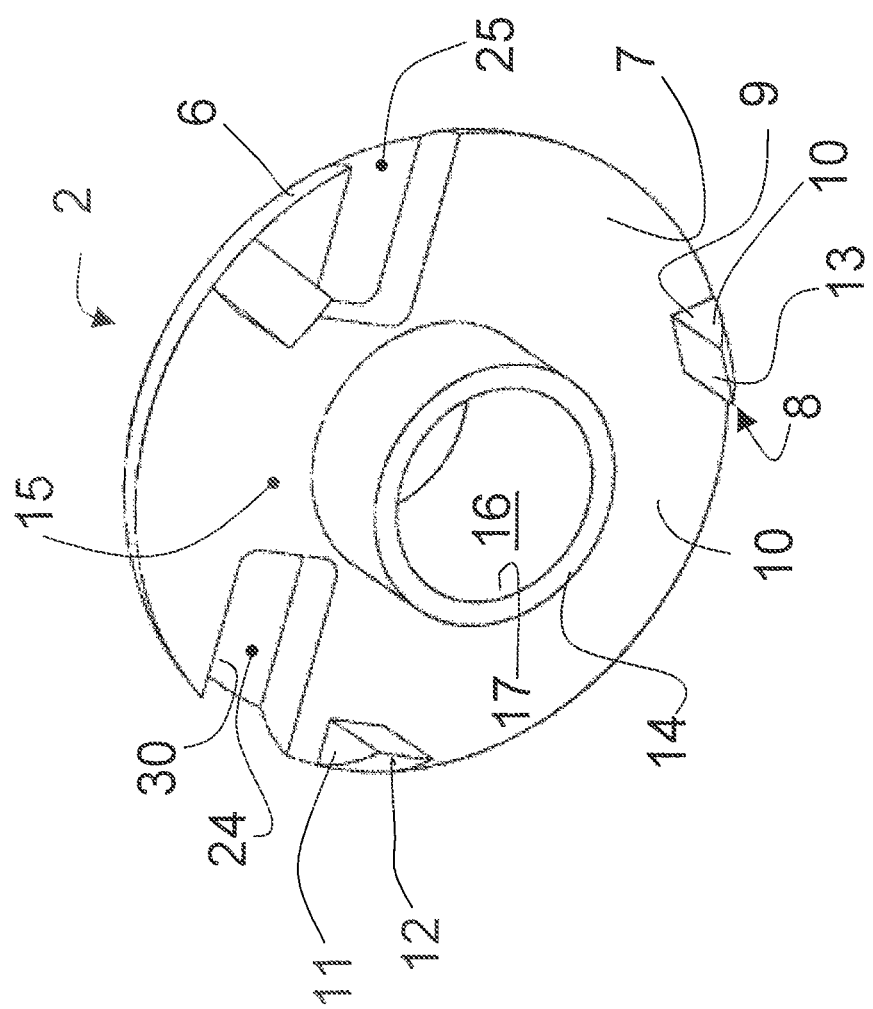
FIG. 2 is a three-quarter bottom perspective view of the base member of the soft tissue fixation device of FIG. 1.

In another preferred embodiment illustrated in FIG. 2, a sleeve 14 will extend downward from the center section 15 of bottom surface 7. Sleeve 14 will have an outside diameter that permits its snug insertion into a channel drilled into the femur bone. Sleeve 14 will also form a passageway 16 that will provide protection to the graft being attached to the bone. It is preferred that all edges of sleeve 14 that may be contacted with the graft be rounded and smooth to prevent cutting or tearing of the graft. Passageway 16 extends along the vertical center axis of base member 2 and sleeve 14. Passageway 16 is shaped to permit the graft to pass through the passageway 16, but preferably has no sharp corners that might damage the graft: that is held against the passageway wall 17. The top surface 4 is also provided with a notch 18 that extends from passageway 16 to the perimeter 19 of top surface 4. The notch 18 should have a width to accommodate at least a substantial portion of the graft. Preferably, notch 18 will also have a depth to accommodate at least a substantial portion of the graft to permit a lower profile design of fixation device 1. It is also preferred that the upper edge sections 20 and 21 of the side walls 22 and 23, respectively, will be rounded and smooth so as to present no sharp edges that would injure the graft when the graft: is pressing against the walls forming notch 18.

Figure 3:
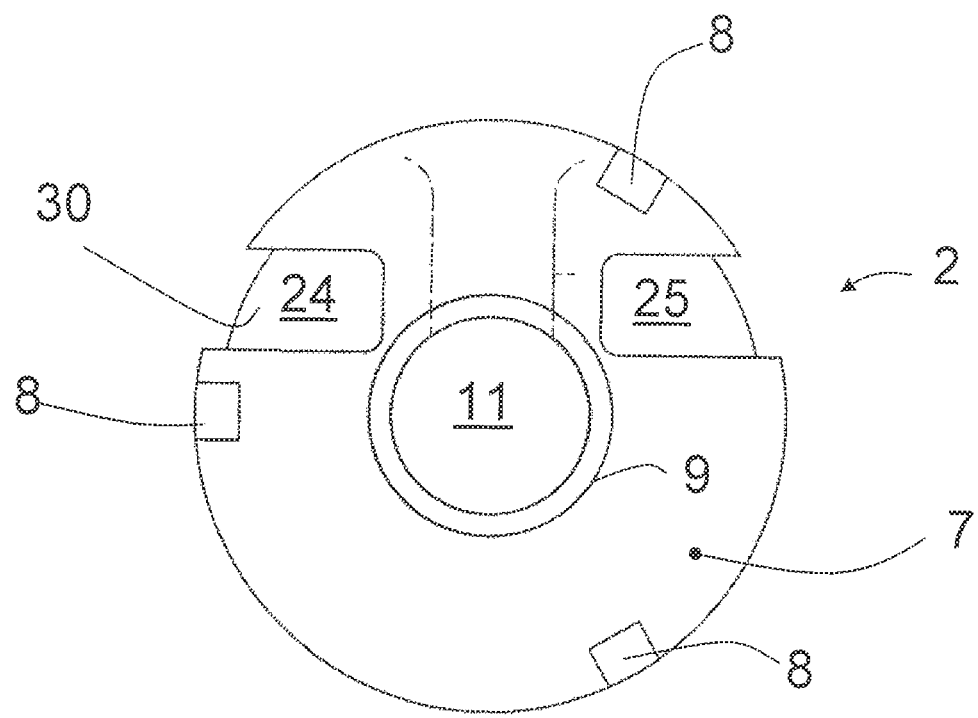
FIG. 3 is a bottom view of the base member of the soft tissue fixation device of FIG. 1.

As illustrated in FIGS. 2 and 3, bottom surface 7 of base member 2 is provided with two aligned notches 24 and 25, respectively. Notches 24 and 25 are constructed to accommodate the attachment of affixing member 3, and more preferably the positioning of affixing member 3 over at least a portion of top surface notch 18.

Figure 4:
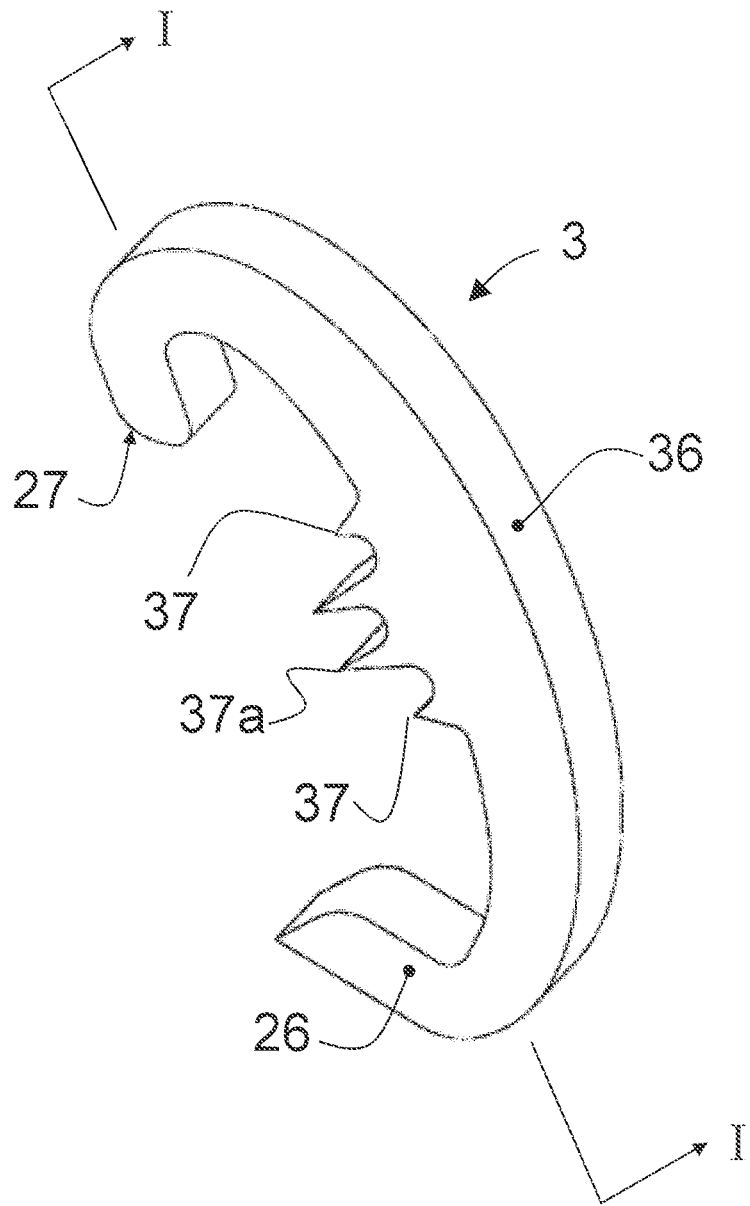
FIG. 4 is a three-quarter perspective view of the clip member forming the soft tissue fixation device of FIG. 1.
Figure 5:
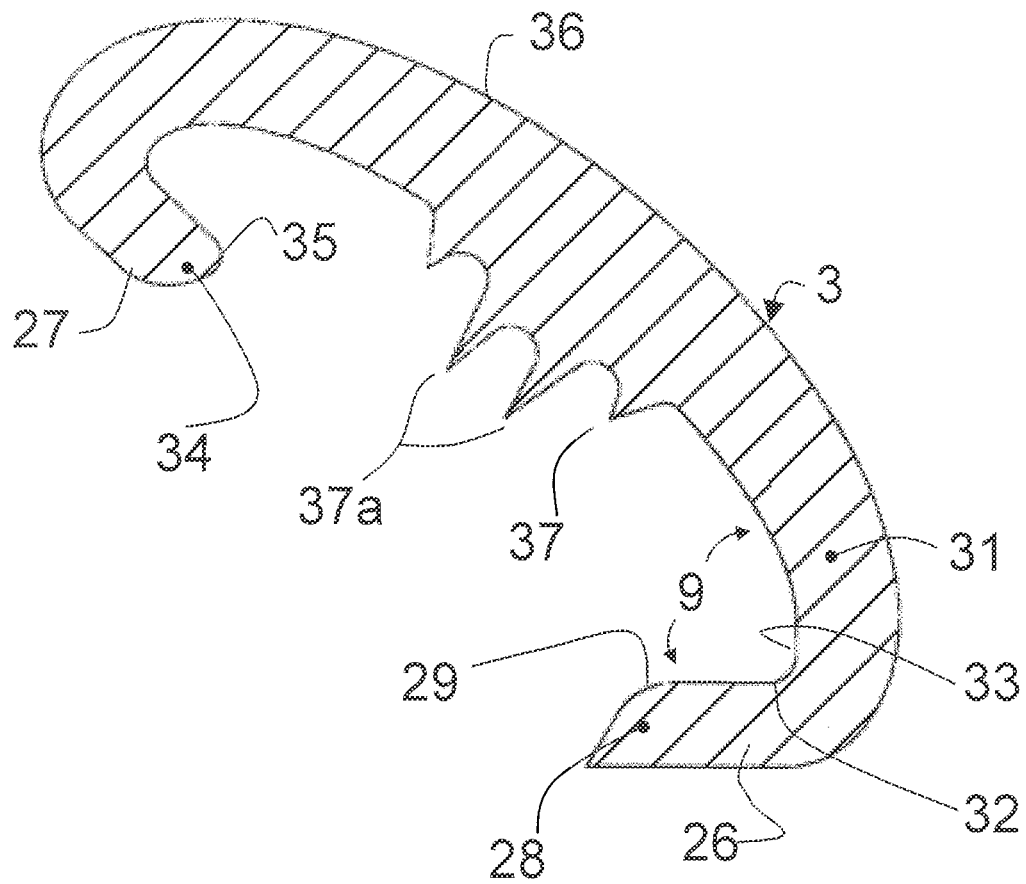
FIG. 5 is a cross-sectional view taken along Section Lines I-I of FIG. 4.

As illustrated in FIGS. 4 and 5, affixing member 3 is constructed having opposing curved end sections 26 and 27. End section 26 includes with a leg member 28 having a flat upper surface 29 that can be positioned on the flat floor surface 30 of notch 24 and of a length to prevent leg member 28 from slipping out of notch 24. The second leg member 31 of end section 26 forms an acute angle "α" with leg member 28. In a more preferred embodiment angle "α" is less than 60°. In a more preferred embodiment a rounded notch 32 is formed by cutting into the interior surfaces 29 and 33 where both leg members 28 and 31 are joined. This construction permits easier flexing of end section 26, yet provides sufficient strength that the end section 26 will not crack when the two leg members 28 and 31 are pressed toward one another. Opposing end 27 is similar constructed except that its leg member 34 is provided with a rounded end 35 to permit easier attachment of affixing member 3.

Affixing member 3 has a middle section 36 provided with teeth 37, or other similar known grabbing elements, that will extend across and into notch 18 when affixing member 3 is secured to base member 2 to hold the graft in the desired tensioned position. In a preferred embodiment teeth 37 will extend on either side of notch 18 to hold any portion of the graft that may overlap notch 18. In order to facilitate clip closure and/or minimize damage to the soft tissue graft, it is also preferred that the length of the teeth 37 be decreased as they are positioned away from the center teeth 37a.

Figure 6:
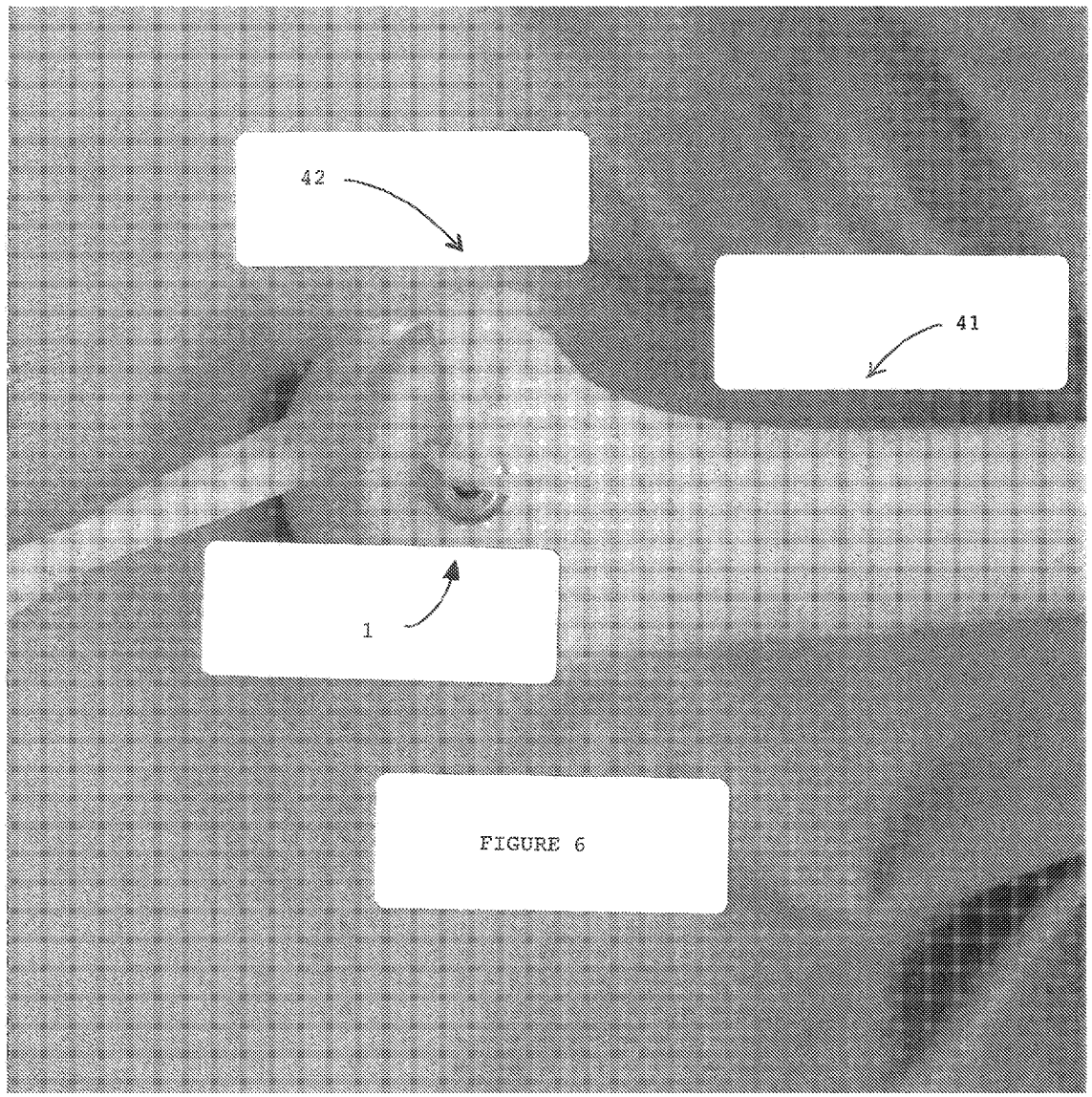
FIG. 6 is a photograph of soft tissue affixed in position by a preferred embodiment of the fixation device of this invention attached to a human femur.

In the surgical procedure utilizing fixation device 1, a tunnel is first drilled from the intra-articular origin of the CrCL to the center of the lateral aspect of each femoral condyle. For a mid-sized dog (approximately 70 lbs.) this canal will be approximately 4.5 mm in diameter. Base member 2 is aligned with the bone tunnel so that its sleeve 14 is over the pilot hole. Base member 2 is then tapped into place with an osteotomy mallet. The graft is passed through the femoral tunnel and sleeve 9. Pivoting end 26 of affixing member 3 is placed in bottom surface notch 24. That portion of the graft extending from the sleeve 14 is positioned across top surface notch 18 of base member 2 and pulled to achieve the desired tensioning. Member 3 is then in one motion pivoted downward until latching end 27 of affixing member 3 is secured in opposite bottom surface notch 19. This action causes teeth 37 of affixing member 3 to grab the graft and secure the graft between base member 2 and affixing member 3 sufficiently to maintain the desired tensioning. FIG. 6 is a photograph of fixation device 1 positioned on a human femur bone 41 with a graft 42 secured to the bone 41 by a fixation device 1 similar to that illustrated in FIGS. 1-5.

Figure 7:
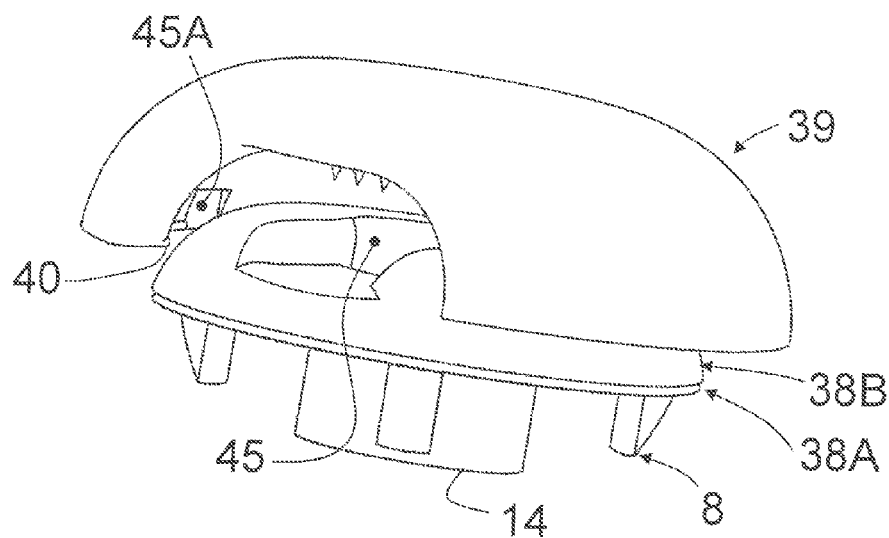
FIG. 7 is an exploded view of an alternate embodiment of the soft tissue fixation device of this invention illustrating the affixing member attached to the base member by hinge means.
Figure 7A:
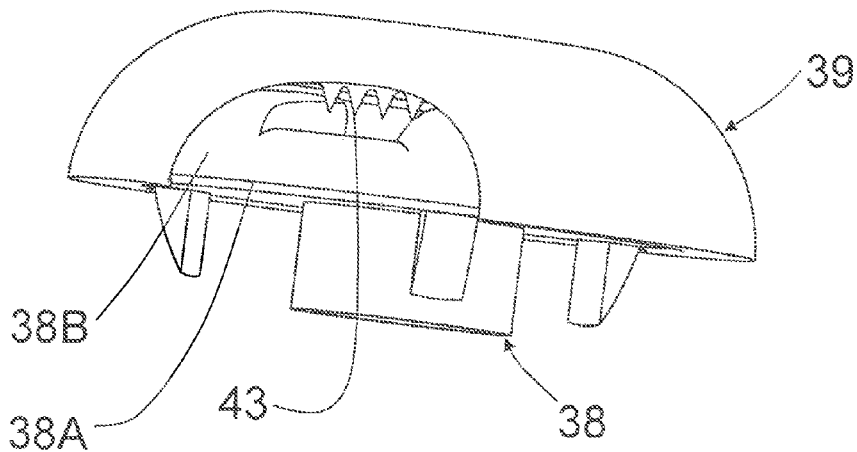
FIG. 7A is a side view of the base member and affixing member in connecting relationship of FIG. 7.
Figure 7B:
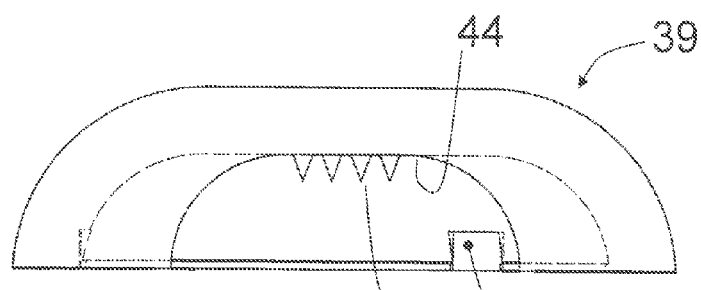
FIG. 7B is a cross-sectional view taken along Section Lines II-II of FIG. 7A.
Figure 7C:
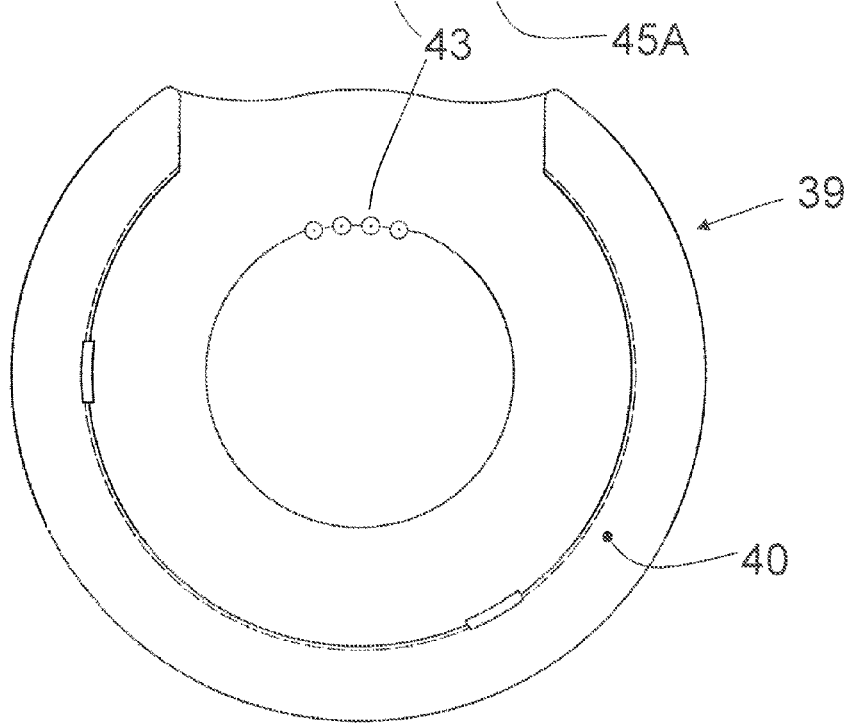
FIG. 7C is a bottom view of FIG. 7A.
Figure 8A:
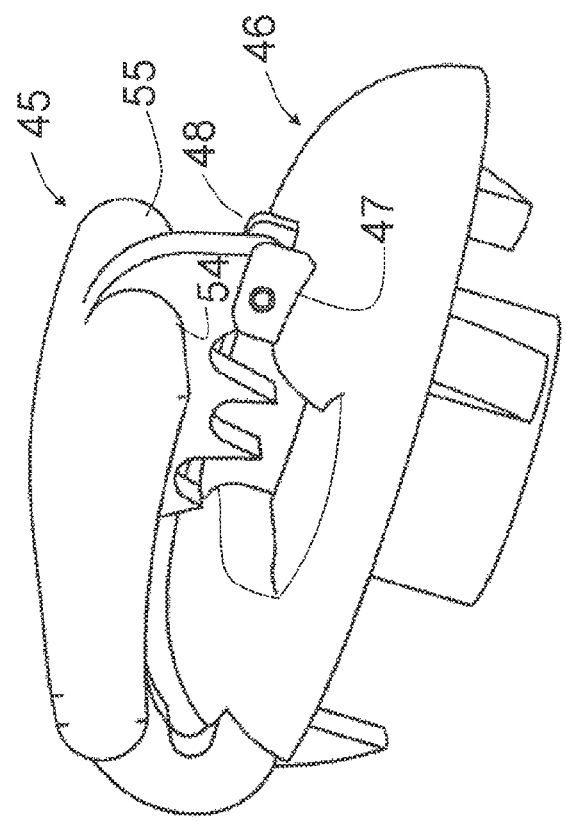
FIG. 8A is a three-quarter perspective view of FIG. 8 wherein the affixing member is engaged with the base member 8.
Figure 8:
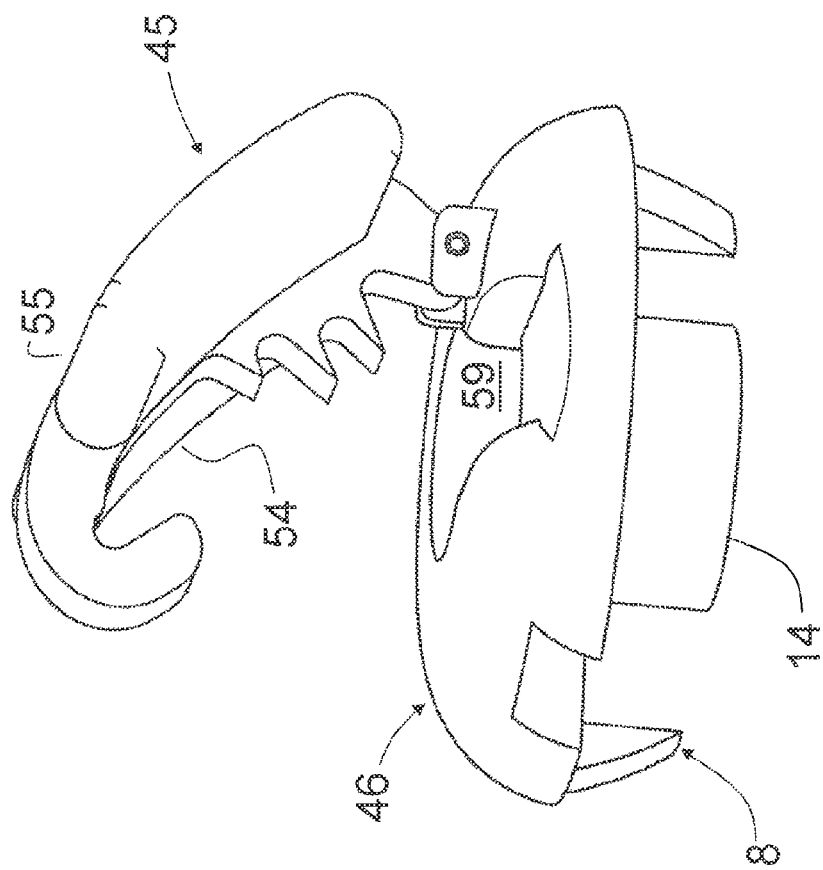
FIG. 8 is a three-quarter perspective view of another alternate embodiment of the soft tissue fixation device of this invention illustrating the affixing member pivotally attachable to the base member.
Figure 8B:
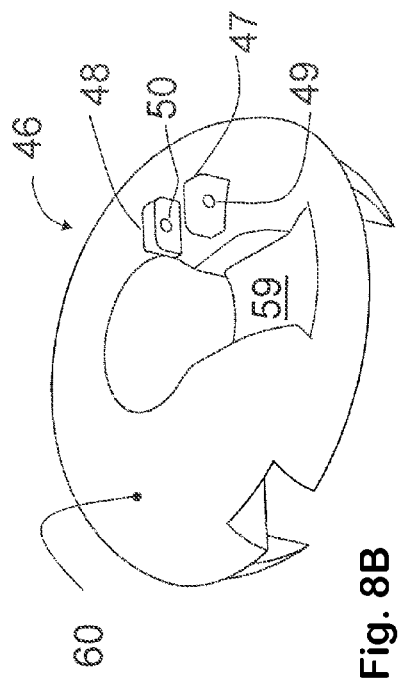
FIG. 8B is a top three-quarter perspective view of the base member of FIG. 8.
Figure 8D:
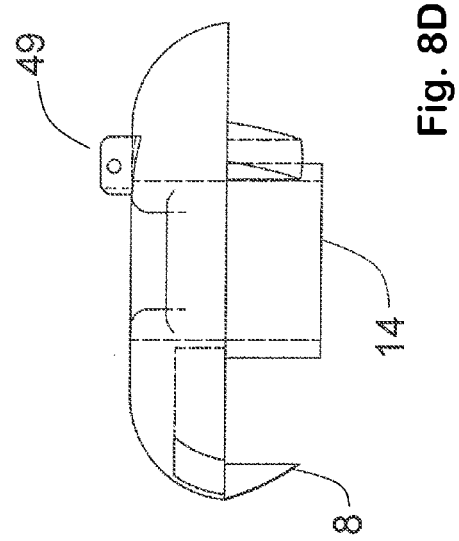
FIG. 8D IS side view of the base member of FIG. 8 without the affixing member attached.
Figure 8C:
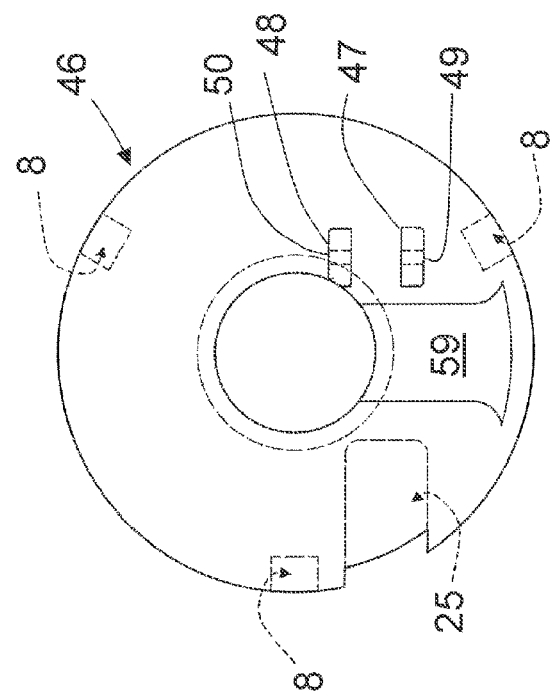
FIG. 8C is a top view of the base member of FIG. 8 without the affixing member attached.
Figure 8E:
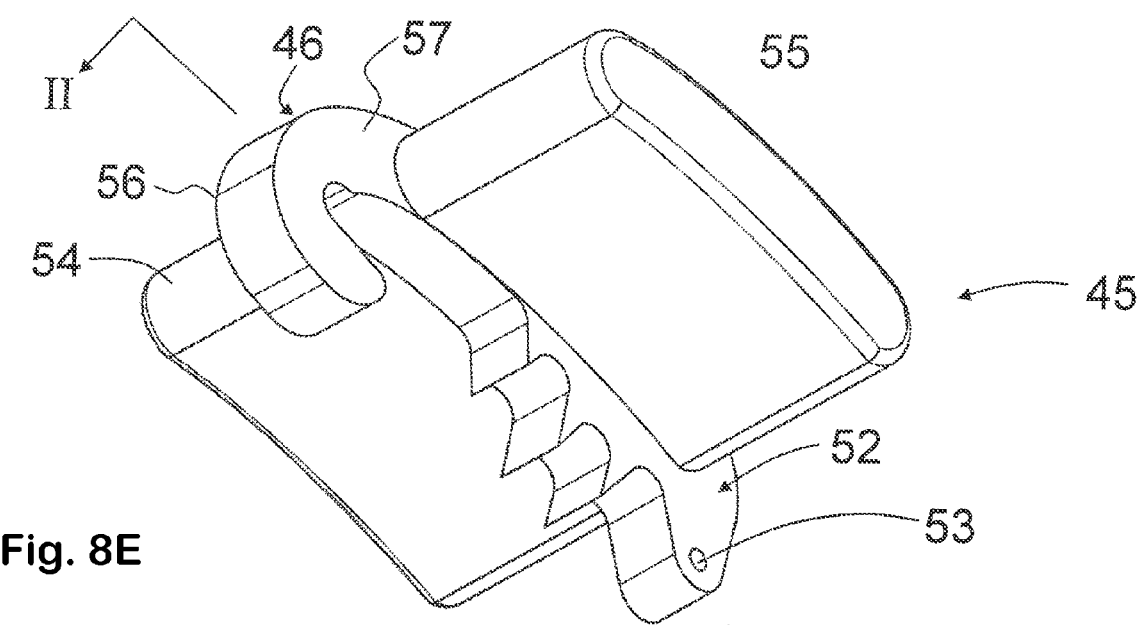
FIG. 8E is a bottom three-quarter perspective view of the affixing member of FIG. 8.
Figure 8F:
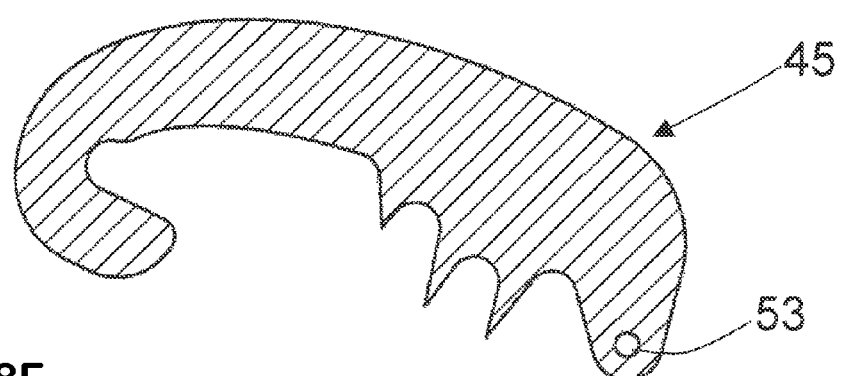
FIG. 8F is a cross-sectional view taken along lines III-III of FIG. 8E.
Figure 9:
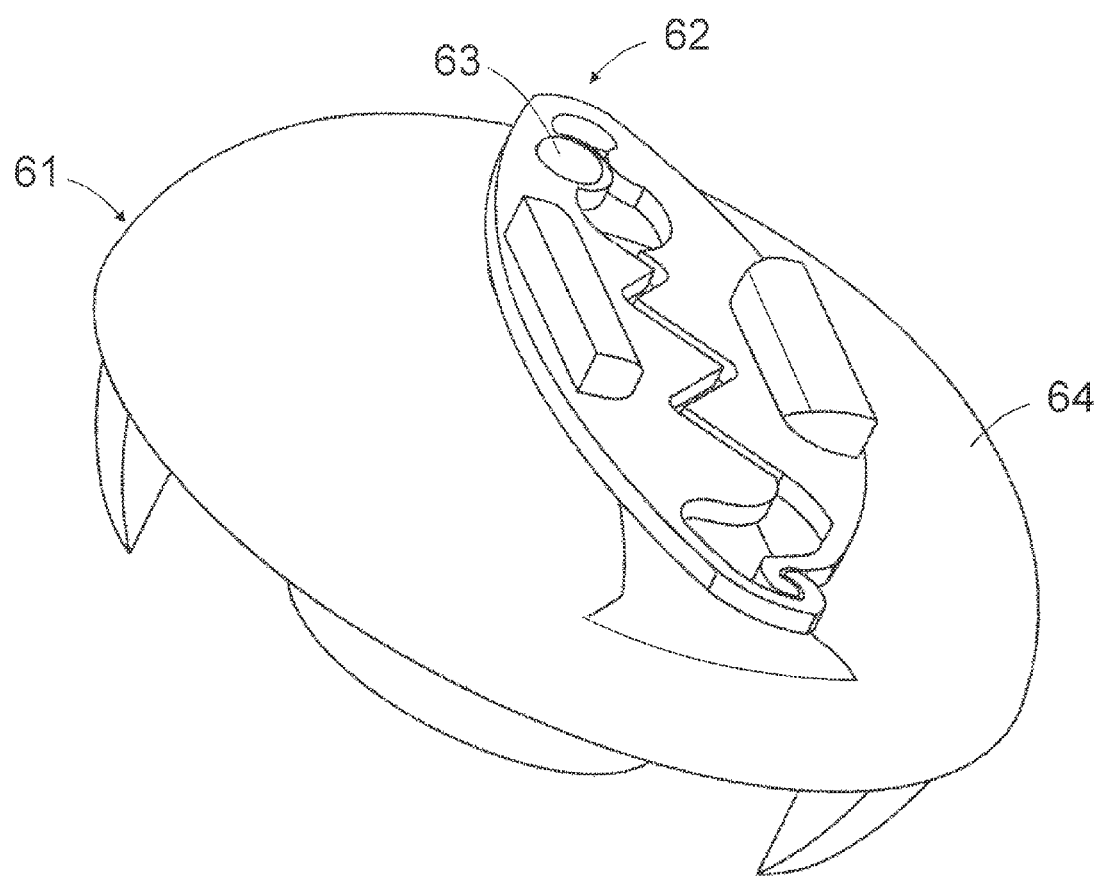
FIG. 9 is a top three-quarter perspective view of an alternate fixation device of this invention.

FIGS. 7-9 illustrate alternate embodiments of the combination of base member 2 and affixing member 3. In FIGS. 7, 7A, 7B and 7C, base member 38 is similarly constructed as base member 2, except there are no notches 24 and 25. Affixing member 39 is shaped to fit over base member 38 and is constructed of material that will permit member 39 to be flexed so that its lower perimeter edge 40 will expand to fit into a groove 38A formed along the lower perimeter area of interior surface 38B of base member 38 to provide a positive attachment between base member 38 and affixing member 39. When spikes 8 are positioned at the perimeter of the base member 38, then affixing member 39 will be provided with corresponding notches 45A to facilitate closure over spikes 8.

Teeth 43 extend downward from the bottom surface 44 of affixing member 39 for positioning in notch 45 shaped in the upper surface of base member 38. Notch 44 is similarly shaped as notch 18 illustrated in FIGS. 1-5. In a preferred embodiment, teeth 43 will also be shaped similarly as teeth 37 in FIGS. 1-5.

FIGS. 8, 8A-8F illustrates another embodiment wherein affixing member 45 is pivotally attached to base member 46 by a conventional pivoting construction. More particularly, base member 46 is provided with parallel separated shoulder members 47 and 48 with each having a connecting aligned passageway 49 and 50, respectively, to accept a pivot pin 51. End section 52 of affixing member 45 is shaped to pass between separated shoulder members 47 and 48. End section 52 is also provided with a passageway 53 that can be aligned with passageways 49 and 50 to permit a pivot pin 51 to extend through each of the passageways to permit affixing member 45 to pivot about pin 51. In a preferred embodiment two pads 54 and 55 extend from opposite sides 56 and 57, respectively, of affixing member 45 to provide a larger surface for the surgeon's hand to contact and provide the force necessary to attach affixing member 45 to base member 46. Shoulder members 47 and 48 are positioned so that the teeth 58 of affixing member 54 will be positioned over notch 59 in the top surface 60 of base member 46 in similar fashion as described with respect to the FIGS. 1-5 embodiment.

FIG. 9 and FIGS. 9A-9C illustrate another embodiment for affixing member 62 to grasp and secure the graft to the bone. In this embodiment affixing member 62 is pivotally secured horizontally to base member 61 by a peg or screw 63 extending upward from the top surface 64 of base member 61 and through opening 65. Affixing member 62 is formed by two leg sections 66 and 67 that are affixed at one of their ends in a manner to be biased to form a gap 68 between the facing serrated edge surfaces 69 and 70 of leg sections 66 and 67, respectively. Each serrated edge surface 69 and 70 is shaped having a series of teeth 71 and 72, respectively, that mate in corresponding valley areas 73 and 74, respectively when leg sections 66 and 67 are forced toward one another as illustrated in FIG. 9A. When leg sections 66 and 67 are separated as illustrated in FIG. 9B, the graft will be extended through gap 68. In a preferred embodiment grasping pads 75 and 76 are positioned on the top surfaces of leg sections 66 and 67, respectively, to assist the surgeon in placing the leg sections 66 and 67 in a closed position to secure the graft at the desired tension. To lock leg sections 66 and 67 in a closed position, opposite end 77 of leg section 66 is configured to form a keeping structure 78 for retaining opposite end 79 of leg section 67. Opposite end 79 is configured to form a latch 80 that operatively fits into keeping structure 78 to reduce gap 68 sufficiently to permit teeth 71 and 72 to hold the graft at the desired tension.

Figure 9E:
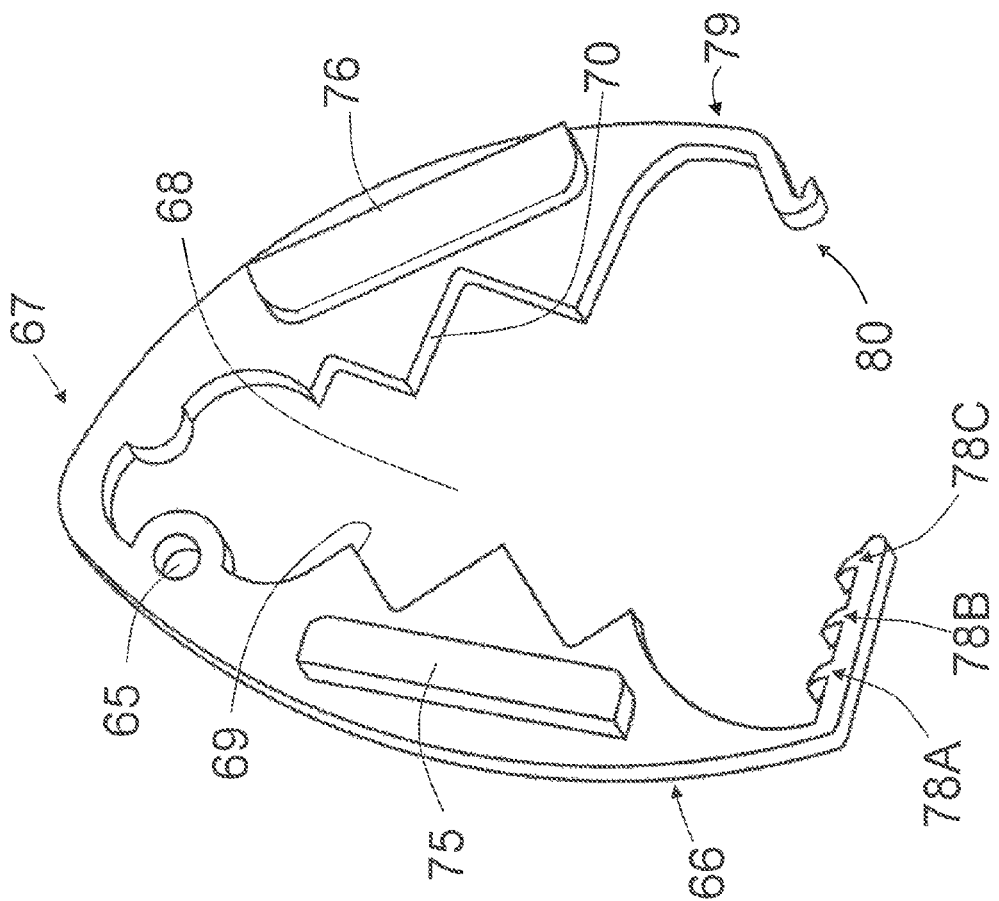
FIG. 9E is a top view of an alternate fixation device in an open position.
Figure 9D:
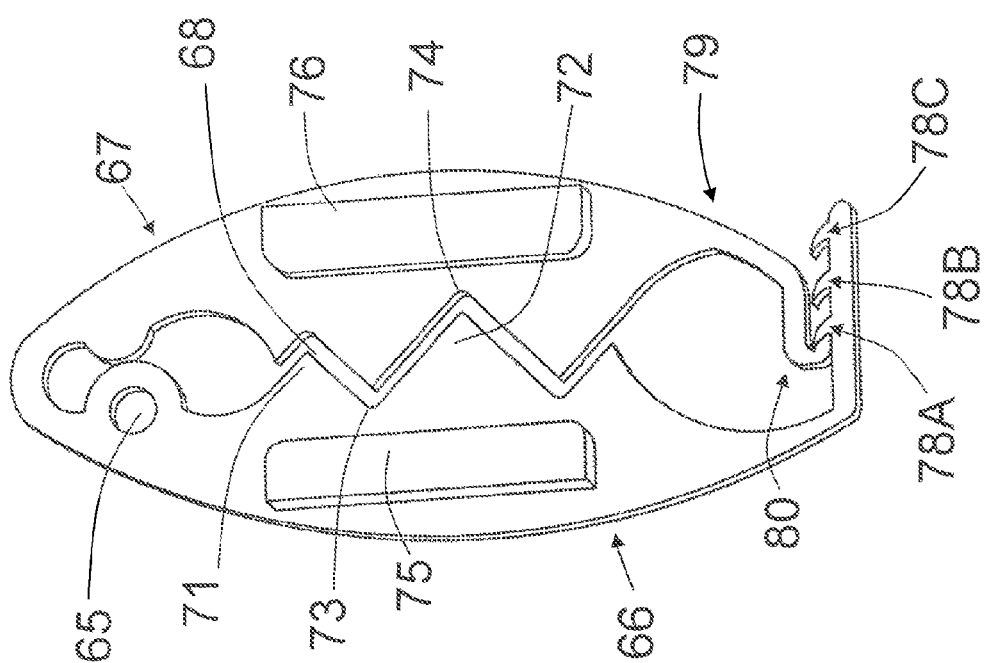
FIG. 9D is a top view of an alternate fixation device having multiple closing positions.

FIGS. 9D-9E illustrate an embodiment of FIG. 9 wherein there are multiple keeping structures 78A, 78B and 78C to permit leg section 67 to be secured to latch 80. This permits variation in the width of gap 68 between teeth 71 and valley 74 in order to facilitate the use of grafts of different thickness. When leg section 67 is in the position shown as 67A, gap 68 will be reduced to ensure that a thinner graft will be securely held in the correct tension. There can of course be more than three different keeping structures 78 to permit different ratcheting positions for securing latch 79.

There are of course other alternate embodiments which are obvious from the foregoing descriptions of the invention which are intended to be included within the scope of the invention as defined by the following claims.

The invention claimed is:

1. A device adapted to affix a soft tissue graft to a bone, said device comprising:
   (a) a base member comprising:
      (i) a top surface, a bottom surface, and a tubular sleeve extending from the bottom surface, wherein the exterior of said tubular sleeve is adapted to permit said tubular sleeve to be inserted into a bone tunnel;
      (ii) a passageway extending through said tubular sleeve, through said bottom surface, and through said top surface, wherein said passageway comprises smooth sides through which a soft tissue graft may pass,
      (iii) an opening in said top surface extending from said passageway,
      (iv) at least one receiving section, and
      (v) at least one element on said bottom surface adapted to secure said base member to bone; and
   (b) an affixing member comprising an attaching section and an affixing section, wherein:
      (i) said attaching section pivotally attaches to said receiving section of said base member, and
      said affixing section is adapted to affix a soft tissue graft that traverses said passageway between said base member and said affixing member.

2. The device of claim 1, wherein said device is flexible.

3. The device of claim 1, wherein said device is bioabsorbable.

4. The device of claim 1, additionally comprising at least one securing member adapted to provide stability for said base member against rotational movement, axial movement, or translational movement.

5. The device of claim 4, wherein said at least one securing member comprises at least one spike adapted to be driven into the bone.

6. The device of claim 1, wherein said device is adapted to present a low profile, to have low impingement on surrounding tissues, and to have low visibility when placed under the skin.

7. The device of claim 1, wherein the top surface of said base member comprises a notched section extending from the passageway to a perimeter of said base member; wherein said notched section is adapted to accommodate at least a portion of the soft tissue graft.

8. The device of claim 1, wherein said base member comprises a notched section; wherein said affixing member has a generally arched shape; and wherein said base member and said affixing member are adapted to accommodate at least a substantial portion of a soft tissue graft within said notched section of said base member and beneath said arched-shape affixing member, without damage to the soft tissue graft.

* * * * *